US008105614B2

(12) United States Patent
Aagaard et al.

(10) Patent No.: US 8,105,614 B2
(45) Date of Patent: Jan. 31, 2012

(54) EXPANDING THE T CELL REPERTOIRE TO INCLUDE SUBDOMINANT EPITOPES BY VACCINATION WITH ANTIGENS DELIVERED AS PROTEIN FRAGMENTS OR PEPTIDE COCKTAILS

(75) Inventors: Claus Aagaard, København S (DK); Jes Dietrich, København NV (DK); Peter Andersen, Brønshøj (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

(21) Appl. No.: 11/823,402

(22) Filed: Jun. 27, 2007

(65) Prior Publication Data

US 2008/0008724 A1 Jan. 10, 2008

Related U.S. Application Data

(60) Provisional application No. 60/817,947, filed on Jun. 30, 2006.

(30) Foreign Application Priority Data

Jun. 28, 2006 (DK) ................................ 2006 00861

(51) Int. Cl.
*A61K 39/04* (2006.01)
*A61K 38/02* (2006.01)
*A01N 25/08* (2006.01)

(52) U.S. Cl. .................................... 424/248.1; 530/300

(58) Field of Classification Search ............... 424/248.1; 350/300, 350
See application file for complete search history.

(56) References Cited

U.S. PATENT DOCUMENTS

| | | | | |
|---|---|---|---|---|
| 4,599,230 | A | 7/1986 | Milich | |
| 4,599,231 | A | 7/1986 | Milich | |
| 4,601,903 | A | 7/1986 | Frasch | |
| 4,608,251 | A | 8/1986 | Mia | |
| 4,975,282 | A | 12/1990 | Cullis et al. | |
| 6,641,814 | B1 * | 11/2003 | Andersen et al. | 424/190.1 |
| 6,649,170 | B1 | 11/2003 | Lindblad et al. | |
| 7,186,412 | B1 * | 3/2007 | Skeiky et al. | 424/190.1 |
| 7,311,922 | B1 * | 12/2007 | Skeiky et al. | 424/248.1 |
| 2005/0191308 | A1 | 9/2005 | Lindblad et al. | |
| 2006/0008519 | A1 | 1/2006 | Davidsen et al. | |

FOREIGN PATENT DOCUMENTS

| | | | |
|---|---|---|---|
| WO | WO 01/16163 | A2 | 3/2001 |
| WO | WO 03/011331 | A2 | 2/2003 |
| WO | WO 2004/002415 | A | 1/2004 |
| WO | WO 2006/002642 | A2 | 1/2006 |
| WO | WO 2006/013162 | A2 | 12/2006 |
| WO | WO2007/085962 | * | 7/2007 |
| WO | WO 2007/125371 | A | 11/2007 |

OTHER PUBLICATIONS

Pan et al. Nucleic acis Research 1999, vol. 27, No. 4, pp. 1094-1103.*
Nonomura et al. The Plant Cell, 2003, vol. 15, pp. 1728-1739.*
Arend et al. Infec. Immun. 2000, vol. 68, No. 6, pp. 3314-3321.*
Louise et al. Infec. Immun, 2002, vol. 70, No. 10, pp. 5446-5453.*
Mansuri et al. J. Org. Chem. 1989, vol. 54, pp. 4780-4785.*
Babu et al, Priming for Virus-Specific CD8+ But Not CD4+ Cytotoxic T Lymphocytes with Synthetic Lipopeptide is Influenced by Acylation Units and Liposome Encapsulation, Vaccine, vol. 13, No. 17, pp. 1669-1676, (Dec. 1995).
Crowe et al., Differential Antigen Presentation Regulates the Changing Patterns of $CD8^+$ T Cell Immunodominance in Primary and Secondary Influenza Virus Infections, J. Exp. Med. vol. 198, No. 3,pp. 399-410, (Aug. 4, 2003).
Davidsen et al, Characterization of Cationic Liposomes Based on Dimethyldioctadecylammonium and Synthetic Cord Factor From *M. tuberculosis* (Trehalose 6,6'-Dibehenate)—A Novel Adjuvant Inducing Both Strong CMI and Antibody Responses, Biochimica et Biophysica Acta, 1718:22-31, (Dec. 2005).
Gosselin et al, Enhanced Antigen Presentation Using Human Fcγ Receptor (Monocyte/Macrophage)-Specific Immunogens, vol. 149, No. 11, pp. 3477-3481, (Dec. 1, 1992).
Harboe et al, B-Cell Epitopes and Quantification of the ESAT-6 Protein of *Mycobacterium tuberculosis*, Infection and Immunity, vol. 66, No. 2, (Feb. 1998).
Kamath et al, Cytolytic $CD8^{30}$ T Cells Recognizing CFP10 are Recruited to the Lung After *Mycobacterium tuberculosis* Infection, J. Exp. Med., vol. 200, No. 11, (Dec. 6, 2004).
Kirby et al, Dehydration-Rehydration Vesicles: A Simple Method for High Yield Drug Entrapment in Liposomes, NatureBioTechnology, 2:979-984, (Nov. 1984).
Krogh et al, Protein Analysis Using Enzymes Immobilized to Paramagnetic Beads, Analytical Biochemistry, 274, pp. 153-162 (Oct. 1999).
Lustig et al, Humoral and Cellular Responses to Native Antigen Following Oral and Parenteral Immunizations with Lipid-Conjugated Bovine Serum Albumin, Cellular Immunology, 24, 164-172, (Jun. 1976).

(Continued)

*Primary Examiner* — Bao Li
(74) *Attorney, Agent, or Firm* — Howson & Howson LLP

(57) ABSTRACT

A convenient way of inducing a broad recognition of dominant and subdominant responses to epitopes of any given antigen of importance for prophylaxis or treatment of a chronic disease is provided. The method involves by immunizing with pools of overlapping fragments (synthetic peptides, e.g., 10-30 mers with 2-20 aa overlap) of the desired antigen in appropriate adjuvants. The T cell repertoire is primed to include not only the immunodominant epitope recognized when the intact molecule is used for immunization and induced by the chronic infection itself, but induce a much broader and balanced response to a number of the subdominant epitopes as well. The vaccination with peptide mix induces a T-cell response that includes response to subdominant epitopes is important for protection against chronic disease that on their own induces a response focused only on immunodominant epitopes. The major advantage of the present invention is that it requires no prior knowledge of the precise localization and identity of the subdominant epitopes and their recognition in a human population, but expands the T-cell repertoire and thereby the total number of epitopes recognized by specific T cells primed by vaccination from a few immunodominant epitopes to a multiple of epitopes.

15 Claims, 12 Drawing Sheets

OTHER PUBLICATIONS

McMichael and Phillips, Escape of Human Immunodeficiency Virus From Immune Control, Annu. Rev. Immunol. 15:271-96, (Apr. 1997).

Mowat et al, Immune-Stimulating Complexes Containing Quil A and Protein Antigen Prime Class U MHC-Restricted T Lymphocytes in Vivo and are Immunogenic by the Oral Route, Immunology, 72, pp. 371-322, (Mar. 1991).

Munoz et al, The Covalent Coupling of HAV-VP3 (110-121) Synthetic Peptide to Liposomes: Physicochemical Studies, International Journal of Pharmaceutics, 269:177-184, (Jan. 2004).

Olsen et al, Efficient Protection against *Mycobacterium tuberculosis* by Vaccination with a Single Subdominant Epitope from the ESAT-6 Antigen, Eur. J. Immunol. 30:1724-1732, (Jun. 2000).

Pick, Liposomes with a Large Trapping Capacity Prepared by Freezing and Thawing of Sonicated Phospholipid Mixtures, Archives of Biochemistry and Biophysics, vol. 212, No. 1, pp. 186-194, (Nov. 1981).

Ravn et al, Human T Cell Responses to the ESAT-6 Antigen From *Mycobacterium tuberculosis*, J. Infect. Dis., 179:637-645, (Mar. 1999).

Sette and Fikes, Epitope-Based Vaccines: an Update on Epitope Identification, Vaccine Design and Delivery, Current Opinion in Immunology, 15:461-470, (Aug. 2003).

Stryhn et al, Peptide Binding Specificity of Major Histocompatibility Complex Class I Resolved into an Array of Apparently Independent Subspecificities: Quantitation by Peptide Libraries and Improved Prediction of Binding, Eur. J. Immunol. 26:1911-1918, (Aug. 1996).

Thompson et al, Clustal W: Improving the Sensitivity of Progressive Multiple Sequence Alignment Through Sequence Weighting, Position-Specific Gap Penalties and Weight Matrix Choice, Nucleic Acids Research, vol. 22, No. 22, pp. 4673-4680, (Nov. 1994).

Van Der Most et al, Changing Immunodominance Patterns in Antiviral CD8 T- Cell Responses After Loss of Epitope Presentation or Chronic Antigenic Stimulation, Virology, 315:93-102, (Oct. 2003).

Wherry et al, Viral Persistence Alters CD8 T- Cell Immunodominance and Tissue Distribution and Results in Distinct Stages of Functional Impairment, Journal of Virology, vol. 77, No. 8, pp. 4911-4927, (Apr. 2003).

Wille-Reece et al, Immunization with HIV-1 Gag Protein Conjugated to a TLR7/8 Agonist Results in the Generation of HIV-1 Gag-Specific Th1 and $CD8^+$ T Cell Responses, The Journal of Immunology, 174:7676-7683, (Jun. 2005).

Kurokohchi, K., et al, Use of Recombinant Protein to Identify a Motif-Negative Human Cytotoxic T-Cell Epitope Presented by HLA-A2 in the Hepatitis C Virus NS3 Region, Journal of Virology, vol. 70, No. 1, pp. 232-240, (Jan. 1996).

* cited by examiner

FIG 1A

| | |
|---|---|
| ESAT6 | MTEQQWNFAGIEAAASAIQGNVTSIHSLLDEGKQSLTKLAAAWGGSGSEAYQGVQQKWDATTELNNALQNLARTISEAGQAMASTEGNVTGMFA |
| ESAT6-P1 | MTEQQWNFAGIEAAA |
| ESAT6-P2 | NFAGIEAAASAIQGN |
| ESAT6-P3 | ASAIQGNVTSIHSLL |
| ESAT6-P4 | NVTSIHSLLDEGKQS |
| ESAT6-P5 | SLLDEGKQSLTKLAA |
| ESAT6-P6 | KQSLTKLAAAWGGSG |
| ESAT6-P7 | AAWGGSGSEAYQGVQ |
| ESAT6-P8 | GSEAYQGVQQKWDAT |
| ESAT6-P9 | QQKWDATTELNNAL |
| ESAT6-P10 | TTELNNALQNLART |
| ESAT6-P11 | ALQNLARTISEAGQA |
| ESAT6-P12 | TISEAGQAMASTEGN |
| ESAT6-P13 | QAMASTEGNVTGMFA |

FIG 1B

Δ15-ESAT6

SAIQGNVTSIHSLLDEGKQSLTKLAAAWGGSGSEAYQGVQQKWDATTELNNALQNLARTISEAGQAMASTEGNVTGMFA

| | |
|---|---|
| TB10.4 | MSQIMYNYPAMLGHAGDMAGYAGTLQSLGAEIAVEQAALQSAWQGDTGITYQAWQAQWNQAMEDLVRAYHAMSSTHEANTMAMMARDTAEAAKWGG |
| TB10.4-P1 | MSQIMYNYPAMLGHAGDM |
| TB10.4-P2 | MLGHAGDMAGYAGTLQSL |
| TB10.4-P3 | YAGTLQSLGAEIAVEQAA |
| TB10.4-P4 | EIAVEQAALQSAWQGDTG |
| TB10.4-P5 | SAWQGDTGITYQAWQAQW |
| TB10.4-P6 | YQAWQAQWNQAMEDLVRA |
| TB10.4-P7 | AMEDLVRAYHAMSSTHEA |
| TB10.4-P8 | AMSSTHEANTMAMMARDT |
| TB10.4-P9 | MAMMARDTAEAAKWGG |

FIG 4

CT521 : MLMPKRTKFRKQQKGQFAGLSKGATFVDFGEFGMQTLERGWITSRQIEACRVAINRYLKRKGKVWIRVFPDKSVTKKPAETRMGKGKGAPDHWVVVVRPGRILFEVANVSKEDAQDALRRAAAKLGIRTRFVKRVERV

CT521-P1: MLMPKRTKFRKQQKGQFAGLSK

CT521-P2: KGQFAGLSKGATFVDFGEFGMQT

CT521-P3: VDFGEFGMQTLERGWITSRQIEA

CT521-P4: GWITSRQIEACRVAINRYLKRKG

CT521-P5: AINRYLKRKGKVWIRVFPDKSVT

CT521-P6: IRVFPDKSVTKKPAETRMGKGKG

CT521-P7: KPAETRMGKGKGAPDHWVVVVRP

CT521-P8: PDHWVVVVRPGRILFEVANVSKE

CT521-P9: ILFEVANVSKEDAQDALRRAAAK

CT521-P10: DALRRAAAKLGIRTRFVKRVERV

FIG 10

SEQUENCE LISTING

```
<160> NUMBER OF SEQ ID NOS: 3

<210> SEQ ID NO 1
<211> LENGTH: 94
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Thr Glu Leu
    50                  55                  60

Asn Asn Ala Leu Gln Asn Leu Ala Arg Thr Ile Ser Glu Ala Gly Gln
65                  70                  75                  80
```

-continued

```
Ala Met Ala Ser Thr Glu Gly Asn Val Thr Gly Met Phe Ala
                85                  90


<210> SEQ ID NO 2
<211> LENGTH: 97
<212> TYPE: PRT
<213> ORGANISM: Mycobacterium tuberculosis

<400> SEQUENCE: 2

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

Glx


<210> SEQ ID NO 3
<211> LENGTH: 138
<212> TYPE: PRT
<213> ORGANISM: Chlamydia trachomatis

<400> SEQUENCE: 3

Met Leu Met Pro Lys Arg Thr Lys Phe Arg Lys Gln Gln Lys Gly Gln
1               5                   10                  15

Phe Ala Gly Leu Ser Lys Gly Ala Thr Phe Val Asp Phe Gly Glu Phe
            20                  25                  30

Gly Met Gln Thr Leu Glu Arg Gly Trp Ile Thr Ser Arg Gln Ile Glu
        35                  40                  45

Ala Cys Arg Val Ala Ile Asn Arg Tyr Leu Lys Arg Lys Gly Lys Val
    50                  55                  60

Trp Ile Arg Val Phe Pro Asp Lys Ser Val Thr Lys Lys Pro Ala Glu
65                  70                  75                  80

Thr Arg Met Gly Lys Gly Lys Gly Ala Pro Asp His Trp Val Val Val
                85                  90                  95

Val Arg Pro Gly Arg Ile Leu Phe Glu Val Ala Asn Val Ser Lys Glu
            100                 105                 110

Asp Ala Gln Asp Ala Leu Arg Arg Ala Ala Ala Lys Leu Gly Ile Arg
        115                 120                 125

Thr Arg Phe Val Lys Arg Val Glu Arg Val
    130                 135
```

EXPANDING THE T CELL REPERTOIRE TO INCLUDE SUBDOMINANT EPITOPES BY VACCINATION WITH ANTIGENS DELIVERED AS PROTEIN FRAGMENTS OR PEPTIDE COCKTAILS

CROSS-REFERENCE TO RELATED APPLICATIONS

This application claims the benefit under 35 USC 119(e) of prior U.S. Provisional Patent Application No. 60/817,947, filed Jun. 30, 2006.

BACKGROUND OF THE INVENTION

The present invention provides a vaccine against chronic diseases such as a bacterial, viral or parasitic infection or cancer, a method of making such vaccines and prophylaxis and treatment of chronic disease.

Compared to the limited number of diseases where vaccines are currently available, a very large number have so far escaped attempts to develop efficient vaccines. A common characteristic for many of these infectious diseases as well as cancer is that they develop slowly and manifest themselves as chronic diseases where the disease is maintained for years in the face of an existing host immune response. This often eventually results in immunopathology that is some cases, such as *Chlamydia trachomatis*, is the real cause of the human disease such as inflammatory scarring of the oviduct resulting in infertility. For some diseases such as *Mycobacterium* (M.) *tuberculosis* infection (TB), a vaccine exists. However, while the vaccine may prevent the acute manifestations of the disease, the bacteria is not cleared and a chronic or latent disease is established. TB runs essentially through 3 phases. During the acute phase, the bacteria proliferate in the organs, until the immune response increases to the point at which it can control the infection, whereupon the bacterial load peaks and starts declining. After this, a chronic or latent phase is established where the bacterial load is kept stable at a low level. In this phase *M. tuberculosis* goes from active multiplication to a state of slow or non-replicating persistence. In some cases such as TB, the infection can suddenly reactivate and overt disease will result. The factors that lead to this reactivation are largely unknown. In other cases such as *Chlamydia*, the infection may remain a symptomatic but the ongoing inflammatory process cause later clinical manifestations such as infertility.

The immune response to many of these difficult diseases includes both humoral and cell-mediated immunity (CMI) components. The CMI response is directed to a hierarchy of T-cell antigens and epitopes from the pathogen. The epitopes are amino acid (aa) stretches of 7-9 aa (MHC I) and 12-15 aa (MHC II) (1). In chronic viral disease such as human immunodeficiency virus (HIV), and chronic bacterial disease such as TB, as well as in cancer, the hierarchy of epitope responses change over time and responses to a few immunodominant epitopes which gradually constitute a large part of the total T-cell response, whereas a large number of other epitopes that all have the potential to bind the MHC class I or II antigen presentation molecules are subdominant or even cryptic resulting in T-cell responses at levels close to or below the detection level (2-6). If induced by vaccination (without competition from dominant epitopes), responses to such subdominant epitopes have been reported to be protective (e.g., in TB (7)), indicating that the epitopes are indeed expressed during the natural infection and can be recognized by effector cells on the invading pathogen. Studies indicate a major concern for current vaccine development is that subdominant epitope responses may have advantages compared to responses to immunodominant epitopes in HIV where escape mutants lack immunodominant epitopes and are therefore not seen by the immune system (8).

The utilization of subdominant T-cell epitopes in the design of vaccines has so far been hampered by two major roadblocks: i) the need for a large panel of different epitopes to cover a diverse human population due to the variation of individual epitopes recognized by individuals with different HLA composition; ii) the need to identify subdominant epitopes to which only low-level T-cell responses close to or below the detection level of immunological assays (e.g., the enzyme-linked immunospot (ELISPOT) assay) are found.

Olsen, et al. (7) describes that a vaccine based on one subdominant epitope of ESAT6 can protect against TB. However, a mix of overlapping peptides spanning the entire region of ESAT6 was not used in this study.

In International Patent Application Publication No. WO 01/016163, a vaccine against virus comprising a peptide mix consisting of peptides that activate T cells regardless of their HLA genotype is described. This application teaches the use of peptide mixes from Hepatitis B to enable a broad coverage when applied for the vaccination of a genetically diverse human population thereby circumventing the non-responders found when immunizing with single peptides. This invention does not teach the peptide driven expansion of T cells directed against subdominant T-cell epitopes relevant for the preventive and therapeutic vaccination against chronic bacterial diseases as taught in the present invention.

In International Patent Application Publication No. WO 03/011331, a prime-boost vaccine is disclosed. To prevent an increased response to dominant epitopes and decreased response to subdominant epitopes, priming is achieved by a DNA or viral vector encoding a string of epitopes. Following the priming stage, the epitopes are used individually, in separate constructs or carried on separate vehicles, to boost the response as opposed to being administered as a single poly-epitope DNA or viral construct.

SUMMARY OF THE INVENTION

The present invention discloses a vaccine against chronic diseases such as a bacterial, viral or parasitic infection or cancer comprising a peptide mixture of overlapping peptides spanning the whole amino acid sequence of a protein that is expressed during the chronic phase of the disease such as a chronic infection caused by a bacteria, a persistent virus or parasite or from proteins expressed in malignant tumors, a method of making such vaccines and prophylaxis and treatment of chronic disease.

The present invention use stretches of amino acid sequences, spanning a whole protein, in a peptide mixture with an overlap of 6-20 amino acids for priming and optionally boosting with the whole protein as an adjuvanted subunit vaccine or expressed in viral delivery systems for maximal induction of humoral responses as well.

The present invention provides vaccines inducing broad recognition of dominant and subdominant responses to any given antigen. The vaccine comprises pools of overlapping fragments of the desired antigen in appropriate adjuvants. The T-cell repertoire is thereby expanded to include not only the immunodominant epitope recognized when the intact molecule is used for immunization and induced by the chronic infection itself, but also to induce a much broader and balanced response to a number of the subdominant epitopes as well. One significant advantage of the present invention is that it requires no prior knowledge of the precise identity of the subdominant epitopes and their recognition in a human population but expands the T-cell repertoire and thereby the total number of target specific T cells primed by vaccination from a few immunodominant epitopes and to multiple epitopes. The resulting T-cell response to subdominant epitopes is important for protection against chronic diseases that on their own induces a response focused only towards immunodominant epitopes. For chronic disease controlled by humoral immunity the T helper cell response primed by the peptide mix may conveniently be boosted by the full size protein for maximum induction of an antibody response as well.

Other advantages of the invention will be apparent from the detailed description of the invention.

BRIEF DESCRIPTION OF THE DRAWINGS

FIG. 1A provides an overview of the ESAT-6 (SEQ ID NO: 1) overlapping peptides: ESAT6-P1 (amino acids 1 to 15 of SEQ ID NO: 1); ESAT6-P2 (amino acids 7 to 21 of SEQ ID NO: 1); ESAT6-P3 (amino acids 15 to 29 of SEQ ID NO: 1); ESAT6-P4 (amino acids 21 to 35 of SEQ ID NO: 1); ESAT6-P5 (amino acids 27 to 41 of SEQ ID NO: 1); ESAT6-P6 (amino acids 33 to 47 of SEQ ID NO: 1); ESAT6-P7 (amino acids 41 to 55 of SEQ ID NO: 1); ESAT6-P8 (amino acids 47 to 61 of SEQ ID NO: 1); ESAT6-P9 (amino acids 55 to 68 of SEQ ID NO: 1); ESAT6-P10 (amino acids 61 to 74 of SEQ ID NO: 1); ESAT6-P11 (amino acids 67 to 81 of SEQ ID NO: 1); ESAT6-P12 (amino acids 74 to 88 of SEQ ID NO: 1); and ESAT6-P13 (amino acids 80 to 94 of SEQ ID NO: 1).

FIG. 1B provides the amino acid sequence of Δ15-ESAT-6 (amino acids 16 to 94 of SEQ ID NO: 1).

FIG. 4 provides a table of TB10.4 (SEQ ID NO: 2) with its overlapping peptides: TB10.4-P1 (amino acids 1 to 18 of SEQ ID NO: 2); TB10.4-P2 (amino acids 11 to 28 of SEQ ID NO: 2); TB10.4-P3 (amino acids 21 to 38 of SEQ ID NO: 2); TB10.4-P4 (amino acids 31 to 48 of SEQ ID NO: 2); TB10.4-P5 (amino acids 41 to 58 of SEQ ID NO: 2); TB10.4-P6 (amino acids 51 to 68 of SEQ ID NO: 2); TB10.4-P7 (amino acids 61 to 78 of SEQ ID NO: 2); TB10.4-P8 (amino acids 71 to 88 of SEQ ID NO: 2); and TB10.4-P9 (amino acids 81 to 96 of SEQ ID NO: 2).

FIG. 10 provides an overview of the CT521 (SEQ ID NO: 3) overlapping peptides: CT521-P1 (amino acids 1 to 22 of SEQ ID NO: 3); CT521-P2 (amino acids 14 to 36 of SEQ ID NO: 3); CT521-P3 (amino acids 27 to 49 of SEQ ID NO: 3); CT521-P4 (amino acids 40 to 62 of SEQ ID NO: 3); CT521-P5 (amino acids 53 to 75 of SEQ ID NO: 3); CT521-P6 (amino acids 66 to 88 of SEQ ID NO: 3); CT521-P7 (amino acids 77 to 99 of SEQ ID NO: 3); CT521-P8 (amino acids 90 to 112 of SEQ ID NO: 3); CT521-P9 (amino acids 102 to 124 of SEQ ID NO: 3); and CT521-P10 (amino acids 116 to 138 of SEQ ID NO: 3).

DETAILED DESCRIPTION OF THE INVENTION

Figure 2B:
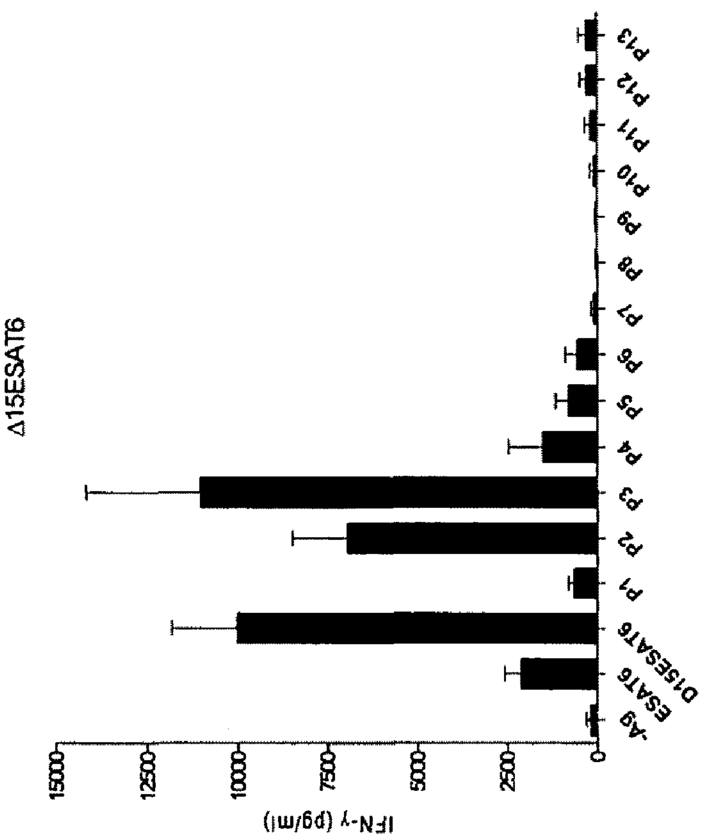
FIGS. 2A and 2B illustrate the immunogenicity of ESAT6 and Δ15ESAT6 in splenocytes. Groups of F1 (Balb/cxC57BL/6) mice were subcutaneously vaccinated three times at two-week intervals with either saline, ESAT6 (FIG. 2A) or Δ15ESAT6 (FIG. 2B) in DDA/TDB. Three weeks after the final vaccination, spleen cells were analyzed by ELISA for INF-γ secretion following stimulation with 1 microgram/ml ESAT6, Δ15ESAT6 or one of the 13 overlapping peptides covering the ESAT6 sequence (P1-P13 as indicated in the figure, also shown in FIG. 1).

The present invention discloses a vaccine against a chronic disease such as a bacterial, viral or parasitic infection or cancer comprising a peptide mixture consisting of adjacent overlapping peptides spanning the whole amino acid sequence of a protein that is expressed during the chronic phase of the disease.

The present invention discloses the use of a mixture of overlapping peptides derived from an antigenic protein and/or the nucleic acid encoding these peptides for a vaccine against a chronic disease such as a bacterial, viral or parasitic infection or cancer.

The peptides are 10 to 30 amino acids long, preferably 12-20 amino acids long where the overlap with the adjacent peptide is 6-20 amino acids, and more preferably 10-12 amino acids.

The antigenic protein which the peptide mixture spans is chosen among proteins that are expressed during the chronic phase of a disease and induces a cell mediated immune response in the case of chronic disease.

In one embodiment, the protein is selected from a bacteria such as a virulent mycobacteria, e.g. by *Mycobacterium tuberculosis, Mycobacterium africanum* or *Mycobacterium bovis, Mycobacterium leprae* or *Chlamydia trachomatis* or a virus such as hepatitis B or C or a parasite such as *Leishmania* or the malaria causing parasite *Plasmodium falciparum* or from molecules expressed in malignant tumours.

The peptides are not restricted to but preferably from a protein selected from *M. tuberculosis* such as ESAT6, Ag85A, Ag85B or TB10.4 or from *Chlamydia trachomatis* such as CT184, CT521, CT443, CT520, CT521, CT375, CT583, CT603, CT610 or CT681 or from a hepatitis B or C or from *Plasmodium falciparum* such as Msp1, Msp2, Msp3, Ama1, GLURP, LSA1, LSA3 or CSP.

The invention also discloses a method for preparing a peptide mixture according to the invention by proteolytic cleavage of the protein with two or more proteolytic cleavage agents such as proteolytic enzymes such a trypsin, V-8 protease, AspN (cleaves N-terminal to aspartic acid) or chymotrypsin or chemical agents such as cyanogen bromide (CNBr) or BNPS-skatole [3-bromo-3-methyl-2-(o-nitrophenylsulfenyl)indolenine)].

The peptide mixture according to the invention can be used for preparing a vaccine against a chronic disease such as a bacterial, viral or parasitic infection or cancer. The vaccine can optionally comprise a delivery system such as an adjuvant. The adjuvant is preferably a based on cationic liposomes such as dimethyldioctadecylammonium bromide/Trehalose dibehenate (DDA/TDB). The peptide mixture used for vaccination can be mixed with preformed liposomes or each peptide can be mixed with the preformed liposomes, the individual peptides formulated in the liposomes are then mixed before immunization.

Each peptide in the peptide mixture can preferably be individually mixed with the liposome prior to making the peptide mixture for optimal interaction with individual antigen presenting cells from the immune system thereby ensuring maximum responses to all epitopes from the molecule.

The invention also discloses a method and vaccine for prophylaxis or therapeutic treatment of a chronic disease in an animal, including a human being, comprising administering to the animal the vaccine of the invention. Optionally the prophylaxis or treatment is boosted by administering a second vaccine comprising the full size protein spanned by the peptide mixture in an adjuvant or expressed in a viral delivery system or as a pure DNA vaccine for optimal boosting a CMI as well as a humoral response.

The invention further discloses a vaccine in which the amino acid sequence is lipidated or conjugated directly to TLR agonist such as CPG so as to allow a self-adjuvanting effect of the polypeptide.

The preferred embodiment of the invention is a vaccine comprising a peptide mixture of the invention preferably with an adjuvant as described above.

DEFINITIONS

Chronic Disease

A chronic disease is a long-lasting or recurring disease. The term chronic describes the course of the disease, or its rate of onset and development. A chronic course is distinguished from a recurrent course; recurrent diseases relapse repeatedly, with periods of remission in between. Chronic infections can be caused by bacteria, e.g. *Mycobacteria* sp. or *Chlamydia* sp. among others, by virus e.g. Hepatitis or HIV, by a parasite, e.g., a malaria causing parasite or *Leishmania* or by diseases such as cancer, diabetes etc.

Peptides

The word "peptide" in the present invention should have its usual meaning. That is an amino acid chain of any length being a part or fragment of a protein, wherein the amino acid residues are linked by covalent peptide bonds.

The peptide may be chemically modified by being glycosylated, by being lipidated (e.g., by chemical lipidation with palmitoyloxy succinimide as described by (9), labeling with PAM3Cys (18) or with dodecanoyl chloride as described by (10)), by comprising prosthetic groups, or by containing additional amino acids such as e.g. a his-tag or a signal peptide or by direct conjugation to TLR agonist (e.g. as described by (11)).

Each peptide may thus be characterised by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | G, A, P |
| | | I, L, V |
| | Polar-uncharged | C, S, T, M |
| | | N, Q |
| | Polar-charged | D, E |
| | | K, R |
| AROMATIC | | H, F, W, Y |

A peptide mixture is liquid mixture of fragments of a protein.

A preferred peptide mixture within the present invention is based on a protein from *M. tuberculosis* such as ESAT6, Ag85A, Ag85B or TB10.4 or from *Chlamydia trachomatis* such as CT184, CT521, CT443, CT520, CT521 or CT375 or from a hepatitis virus or from *Plasmodium falciparuman* such as momp, omp, msp1, msp3, ama1 or glurp. It may also be a peptide mixture or proteolytic digest based on a fusion molecule e.g. as previously described as a relevant vaccine constructs against TB in PCT/DK2006/000356. In general all peptide mixtures of proteins inducing a CMI response which can be used in vaccines against chronic disease can be used to induce an increased prophylactic or therapeutic response as a vaccine Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as MHC class II epitopes and therefore especially preferred lengths of the polypeptide fragment used in the inventive method are 18, such as 15, 14, 13, 12 and even 11 amino acid residues. It is expected that the peptides having a length of between 7 and 12 amino acid residues will prove to be most efficient as MHC class I epitopes and therefore especially preferred lengths of the polypeptide fragment used in the inventive method are 11, such as 10, 9, 8 and even 7 amino acid residues.

Epitopes

By T cell epitopes is understood a sequence of amino acids that is recognized by specific T cells through their T cell receptor after presentation by an antigen presenting cell in the context of either MHC class I or II.

A dominant epitope is a sequence of amino acids that, when part of a protein, induce a high T cell response and often the majority of the response to an antigen is directed to a few T dominant T cell epitopes.

A subdominant epitope is a sequence of amino acids that when part of a protein does not induce a strong T cell response, even though the epitopes are immunogenic and able to induce a significant T cell response when isolated from the protein.

By mixture of overlapping polypeptides or protein fragments is understood a mixture of 10 to 30 mers, with a 6-20 amino acid overlap, spanning an entire protein.

Variants

A common feature of the polypeptides of the invention is their capability to induce an immunological response as illustrated in the examples. It is understood that a variant of a polypeptide of the invention produced by substitution, insertion, addition or deletion may also be immunogenic as determined by any of the assays described herein.

Immune Individual

An immune individual is defined as a person or an animal, which has cleared or controlled an infection.

Immune Response

The immune response may be monitored by one of the following methods:

An in vitro cellular response is determined by induction of the release of a relevant cytokine such as IFN-γ or the induction of proliferation in lymphocytes withdrawn from an animal or human being currently or previously infected with virulent mycobacteria or immunized with the relevant peptide mixture. The induction being performed by the addition of the peptide mixture or the immunogenic portion of the mixture to a suspension comprising from $2\times10^5$ cells to $4\times10^5$ cells per well. The cells being isolated from either the blood, the spleen, the lymph nodes, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation is measured by liquid scintillation counting. A positive response is defined as being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for detecting the immune response is the ELISpot method, in which the frequency of IFN-γ producing cells is determined. In an ELIspot plate (MAHA, Millipore) precoated with anti-murine IFN-γ antibodies (PharMingen) graded numbers of cells isolated from either blood, spleen, or lung (typically between 1 to $4\times10^5$ cells/well) are incubated for 24-32 hrs in the presence of the peptide mixture or the immunogenic portion resulting in a concentration of not more than 20 μg per ml. The plates are subsequently incubated with biotinylated anti-IFN-□ antibodies followed by a streptavidin-alkaline phosphatase incubation. The IFN-γ producing cells are identified by adding BCIP/NBT (Sigma), the relevant substrate giving rise to spots. These spots can be enumerated using a dissection microscope. It is also a possibility to determine the presence of mRNA coding for the relevant cytokine by the use of the PCR technique. Usually one or more cytokines will be measured utilizing for example PCR, ELISPOT or ELISA. It will be appreciated by a person skilled in the art that a significant increase or decrease in the amount of any of these cytokines induced by a specific peptide mixture can be used in evaluation of the immunological activity of the polypeptide.

An in vitro cellular response may also be determined by the use of T cell lines derived from an immune individual or an infected person where the T cell lines have been driven with either live bacteria, extracts from the bacterial cell or culture filtrate for 10 to 20 days with the addition of IL-2. The induction being performed by addition of not more than 20 μg peptide mixture per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both-assays a positive response being a response more than background plus two standard deviations.

An in vivo cellular response may be determined as a positive delayed-type hypersensitivity (DTH) response after intradermal injection or local application patch of at most 100 μg of the polypeptide or the immunogenic portion to an individual who is clinically or subclinically infected with a virulent bacterium, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the peptide mixture or the immunogenic portion is absorbed to either a nitrocellulose membrane or a polystyrene surface. The serum is preferably diluted in PBS from 1:10 to 1:100 and added to the absorbed peptide mixture and the incubation being performed from 1 to 12 hours. By the use of labeled secondary antibodies the presence of specific antibodies can be determined by measuring the optical density (OD), e.g., by ELISA where a positive response is a response of more than background plus two standard deviations or alternatively a visual response in a Western blot.

Another relevant parameter is measurement of the protection in animal models induced after vaccination with the peptide mixture in an adjuvant or after DNA vaccination. Suitable animal models include primates, guinea pigs or mice, which are challenged with an infection. Readout for induced protection could be decrease of the bacterial load in target organs compared to non-vaccinated animals, prolonged survival times compared to non-vaccinated animals and diminished weight loss compared to non-vaccinated animals.

Preparation Methods

In general, antigens and DNA sequences encoding such antigens, may be prepared using any one of a variety of procedures.

The peptide mixture can be produced synthetically when the peptide fragment have fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the peptide mixture as defined by the invention for DNA vaccination a host strain such as *E. coli* can be used. Plasmid DNA can then be prepared from cultures of the host strain carrying the plasmid of interest, and purified using, e.g., the QIAGEN Giga-Plasmid column kit (Qiagen, Santa Clara, Calif., USA) including an endotoxin removal step. It is preferred that plasmid DNA used for DNA vaccination is endotoxin free.

Protease Digest of Antigens

A set of overlapping peptides can be made by proteolytic cleavage of the intact protein which can be expressed as a recombinant tagged protein in, e.g., *E. coli*, followed by purification by column chromatography such as metal chelate chromatography. Two or more proteolytic cleavage agents can be selected that will generate different fragments and thereby overlapping peptide cocktail. Proteolytic enzymes such as trypsin, V-8 protease, AspN or chymotrypsin can be used or chemical agents like CNBr or BNPS-skatole. The number of cleavage sites and the length of the fragments generated are determined by the amino acid sequence of the protein and the specific cleavage agent, e.g., Asp-N hydrolyzes proteins at the N-terminal side of aspartic acid and cysteic acid residues. The V-8 protease cleaves at the carboxyl side of glutamic acid in ammonium bicarbonate buffer at pH 7.8. For proteolytic enzymes coupling of the enzyme to beads before cleavage is possible (16), and this coupling will allow removal of the enzyme after completion of the cleavage by centrifugation of the beads. Alternatively, the protease can be removed from the digestion mixture by chromatographic methods such as gel filtration or reversed-phase high performance liquid chromatography (HPLC). After digestion of the protein, mass spectrometry analysis of the digest is performed to confirm that cleavage of the protein has taken place as predicted. Finally, the two digestion mixtures can be combined to form a mixture of overlapping peptides.

Protein Vaccine

A vaccination with a recombinant protein will induce a T cell response towards a limited number of dominant peptide epitopes within this protein. In contrast, vaccinating with a mix of overlapping peptides, spanning the entire amino acid sequence of the protein, will generate a T cell response against an increased number of epitopes being both dominant and sub-dominant peptide epitopes.

The invention pertains to a vaccine composition comprising a peptide mixture according to the invention. In order to ensure optimum performance of such a vaccine composition it is preferred that it comprises an immunologically and pharmaceutically acceptable carrier, vehicle or adjuvant.

An effective vaccine, wherein a peptide mixture of the invention is recognized by the animal, will in an animal model be able to decrease bacterial load in target organs, prolong survival times and/or diminish weight loss after challenge with an infectious organism, compared to non-vaccinated animals either when given as a preventive or therapeutic vaccine.

Suitable vehicles are selected from the group consisting of a diluent and a suspending agent. The adjuvant is preferably selected from the group consisting of DDA, Quil A, poly I:C, aluminum hydroxide, Freund's incomplete adjuvant, IFN-γ, IL-2, IL-12, monophosphoryl lipid A (MPL), Trehalose Dimycolate (TDM), TDB and muramyl dipeptide (MDP).

An adjuvant is defined as a substance that non-specifically enhances the immune response to an antigen. Depending on the nature of the adjuvant it can promote a cell-mediated immune response, a humoral immune response or a mixture of the two. Since the enhancement of the immune response is non-specific, it is well understood in the field that the same adjuvant can be used with different antigens to promote responses against different targets e.g. with an antigen from *M. tuberculosis* to promote immunity against *M. tuberculosis* or with an antigen derived from a tumor, to promote immunity against tumors of that specific kind.

"Liposomes" are defined as closed vesicles structures made up of one or more lipid bilayers surrounding an aqueous core. Each lipid bilayer is composed of two lipid monolayers, each of which has a hydrophobic "tail" region and a hydrophilic "head" region. In the bilayer, the hydrophobic "tails" of the lipid monolayers orient toward the inside of the bilayer, while the hydrophilic "heads" orient toward the outside of the bilayer. Liposomes can have a variety of physicochemical properties such as size, lipid composition, surface charge, fluidity and number of bilayer membranes. According to the number of lipid bilayers liposomes can be categorized as unilamellar vesicles (UV) comprising a single lipid bilayer or multilamellar vesicles (MLV) comprising two or more concentric bilayers each separated from the next by a layer of water. Water soluble compounds are entrapped within the aqueous phases/core of the liposomes opposed to lipophilic compounds which are trapped in the core of the lipid bilayer membranes.

The peptide mixture used for vaccination can be mixed with preformed liposomes as previously described (WO2006002642 which is hereby incorporated as reference) or each peptide can be mixed with the preformed liposomes in the same manner, the individual peptides formulated in the liposomes are then mixed before immunization.

The standard preparation of liposomes is by dissolving the lipids in an organic solvent which is then evaporated to dryness leaving a thin lipid film on the inside of the test tube. The dry lipid film is then hydrated in an appropriate amount of aqueous phase and the mixture is heated to above the phase transition temperature of the lipids and allowed to "swell". The resulting liposomes which consist of multilamellar vesicles (MLV's) are dispersed by shaking the test tube.

Different principles for interaction of a peptide or peptide mixtures to liposomes exist. One method is surface association (by electrostatic or hydrophobic interactions) of the peptides with the liposomes by incubation of the peptides with preformed liposomes (19). It is also possible to make a covalent coupling of peptides to the surface of the liposomes by chemical crosslinking (e.g. as described in reference 20). In addition, the peptides can be encapsulated in the liposomes by different methods. One method is to add the peptides directly into the lipid film followed by rehydration. Another method describes adding the peptides to the buffer used for rehydration of the liposomes from the lipid film. In addition, the peptides can be encapsulated by the dehydration-rehydration method (21) in which a peptide is encapsulated by freeze drying followed by rehydration of the lyophilized liposomes. Alternatively the antigen is encapsulated using the freeze and thaw technique described by Pick (22) and by Bally et al. in U.S. Pat. No. 4,975,282. In this technique vesicles are mixed with the protein antigen and repeatedly snap frozen in liquid nitrogen and warmed to temperatures above the main phase transition temperature of the relevant lipids. The vesicles may be further processed to remove any non-entrapped antigen e.g. by washing and centrifuging.

Finally, the peptide mixture can then be delivered by the liposomes in two ways. The peptides can either be mixed before the interaction with the liposomes or the peptides can be mixed after interaction of the individual peptides with the liposomes as described above.

The peptides can also be encapsulated in the liposomes by adding the peptides to the buffer used for rehydration of the liposomes from a lipid film or on freeze dried form.

The polypeptide may also be chemically modified by being glycosylated, by being lipidated (e.g. by chemical lipidation with palmitoyloxy succinimide as described by Mowat et al. 1991, labeling with PAM3Cys (18) or with dodecanoyl chloride as described by Lustig et al. 1976), by comprising prosthetic groups or by direct conjugation to TLR agonist (e.g., as described by Seder 2006).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (CARBOPOL brand), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in (17) (which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection. When administered to prevent an infection, the vaccine is given prophylactically, before definitive clinical signs or symptoms of an infection are present. Since the current vaccines, e.g., BCG appears to induce an effective, but short-lived immune response, prophylactic vaccines may also be designed to be used as booster vaccines. Such vaccines are given to individuals who have previously received a vaccination, with the intention of prolonging the period of protection.

In instances where the individual has already become infected or is suspected to have become infected, the previous vaccination may have provided sufficient immunity to prevent primary disease, but as discussed previously, boosting this immune response will not help against the latent infection. In such a situation, the vaccine has a particular advantage as a therapeutic vaccine designed for efficacy against the latent stage of infection.

Importantly in chronic diseases such as TB, cancer, hepatitis and HIV, the long term equilibrium between host and pathogen often results in immune responses focused towards a few immuno-dominant epitopes. Inducing a broad balanced response towards a range of epitopes within a given protein can not be achieved by immunizing with the recombinant protein, which would only lead to a response towards a limited number of dominant epitopes. However, in contrast, the present invention teaches that vaccinating with a mix of overlapping peptides does induce a T cell immune response towards a range of epitopes within a given protein. The present invention and the induction of responses to subdominant epitopes therefore are particularly advantageous for these diseases because it can induce an immune response against protective epitopes that are not induced by the chronic disease, or by vaccinating with the given protein in a recombinant full length form. By conventional preventive vaccination or post-exposure in a therapeutic manner the application of the peptide mixture vaccine technology is superior and with much higher activity than conventional vaccines based on full size molecules against these chronic diseases.

Furthermore, for chronic diseases where humoral immunity is important, it is possible to induce an optimal broad T cell response and a maximal B cell response towards the same protein. In this situation, primary immunization is done with a mix of overlapping peptides (in an adjuvant) spanning the entire sequence of a given protein and the boosting is achieved with a second vaccine comprising the same protein in recombinant form in an adjuvant. In this way the broad T cell response against both dominant and subdominant epitopes will enable maximal T helper cell activity and thereby a very strong antibody response. The resulting response is a broad T cell and maximal antibody response towards the same antigen, with particular use against chronic diseases.

The following examples are illustrative only and do not limit the scope of the invention.

EXAMPLES

Example 1

ESAT-6

Figure 2A:
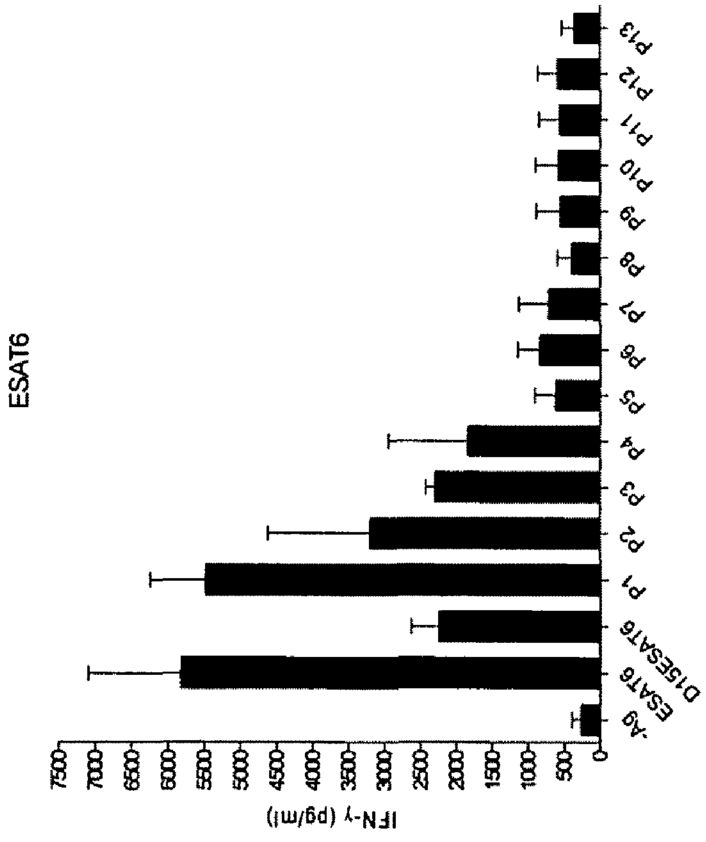

The degree to which the *Mycobacterium tuberculosis*—expressed antigen ESAT-6 contains dominant and subdominant epitopes was examined as follows. Mice were vaccinated with the recombinant protein ESAT-6 3 times at 2 weeks interval and cells were taken two weeks after final vaccination from blood and stimulated with the indicated ESAT-6 peptides (FIG. 1A) [SEQ ID NO:1]. After stimulation, secretion of interferon gamma (IFN-γ), as assessed by ELISA, was determined. The results showed an induction of IFN-γ producing T cells specific for P1 (amino acids 1 to 15 of SEQ ID NO: 1) and to a lesser degree P2 (amino acids 7 to 21 of SEQ ID NO: 1). Removing the immunodominant epitope P1 from ESAT6 (giving the construct named "Δ15-ESAT-6 in which the amino acids 1-15 of ESAT 6 (SEQ ID NO:1) have been deleted" (FIG. 1B)) led to immune recognition of new epitopes, P2 and in particular P3 (FIG. 2). This demonstrated that P1 is a dominant epitope, and that P2 and P3 (amino acids 15 to 29 of SEQ ID NO: 1) constitute subdominant (but immunogenic) epitopes.

Next, whether the subdominant epitopes were able to confer protection against infection with *M. tuberculosis* was examined. Mice were subcutaneously vaccinated three times at two-week intervals with either saline, BCG, DDA/TDB with ESAT6, or Δ15ESAT6. Six weeks after the last vaccination the mice were challenged with virulent *M. tuberculosis*. Six weeks post-challenge, the mice were killed and the bacterial burden (CFU) was measured in the lung.

Figure 3:
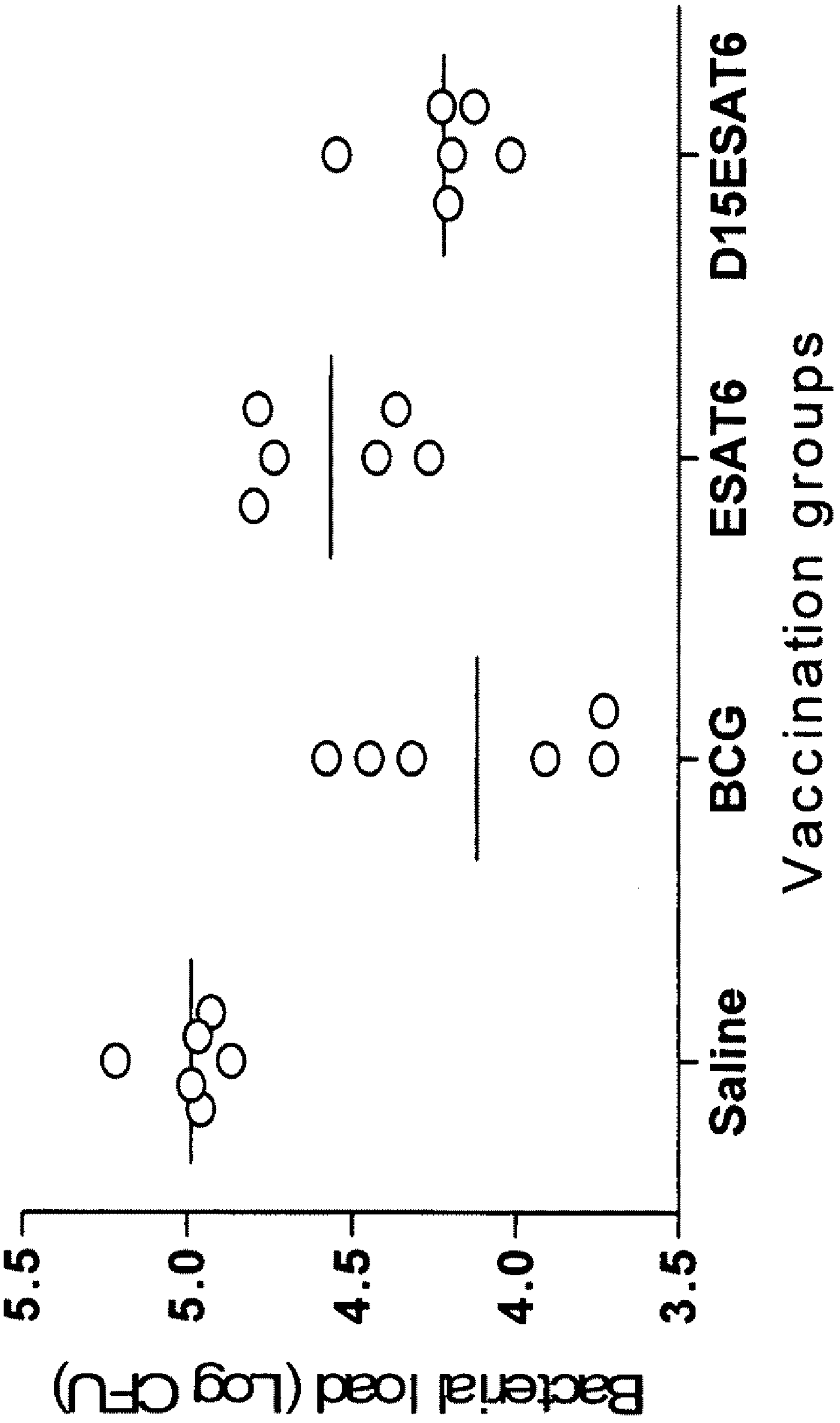
FIG. 3 shows the protective efficacy of ESAT6 and Δ15ESAT6. Groups of F1 (Balb/cxC57BL/6) mice were subcutaneously vaccinated three times at two-week intervals with either saline (column 1), BCG (column 2), ESAT6 (column 3) or Δ15ESAT6 (column 4). Six weeks after the last vaccination the mice were challenged with virulent *M. tuberculosis*. Six weeks post-challenge, the mice were killed and the bacterial burden (colony forming units, CFU) was measured in the lung.

Protection experiments showed that Δ15-ESAT-6 was more protective than ESAT-6 (FIG. 3), indicating that the subdominant peptides (epitopes) P2 and P3 were indeed able to induce an immune response that mediated protection against infection with *M. tuberculosis*.

Figure 11:
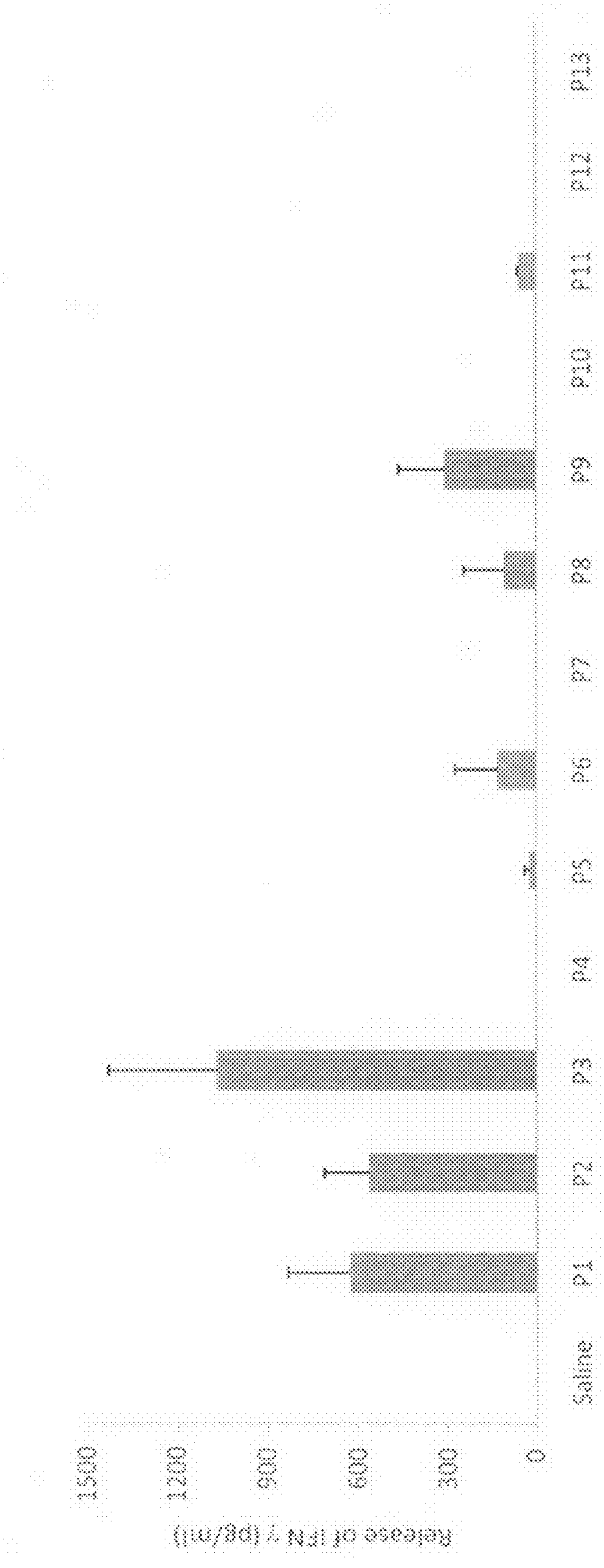
FIG. 11 is a bar chart showing the release of IFN-γ in peripheral blood mononuclear lymphocytes (PBMC) cultured with ESAT-6 peptides. Mice were vaccinated three times at 2-week intervals with a mix of all the ESAT-6 peptides (P1-P13), and the immune response as measured by secretion of IFN-γ, was investigated by culturing blood cells with each of the individual ESAT-6 peptides P1-P13.

Next, whether vaccination with a mix of all overlapping ESAT-6 peptides would lead to a broader recognition of P1-P13 compared to mice vaccinated with the recombinant protein ESAT-6 was examined. Mice were vaccinated three times at 2-week intervals with a mix of all the peptides, and the immune response was investigated by culturing blood cells with each of the individual ESAT-6 peptides P1-P13 (FIG. 11). The results showed that, in contrast to vaccinating with recombinant protein ESAT-6, vaccinating with a mix of ESAT-6 peptides (P1-P13) led to a broader recognition of the peptides (FIG. 11).

To examine whether the broader response towards ESAT-6 was reflected in the protection against infection with *M. tuberculosis*, as compared to the protein induced by vaccination with the recombinant protein ESAT-6, mice were vaccinated three times at 2-week intervals with either ESAT-6 or ESAT-6-peptide mix. 6 weeks after the last vaccination, the mice were subjected to an aerosol challenge with virulent *M. tuberculosis* 10 weeks after the challenge, the mice were killed and the bacterial numbers were determined in the lungs.

Figure 12:
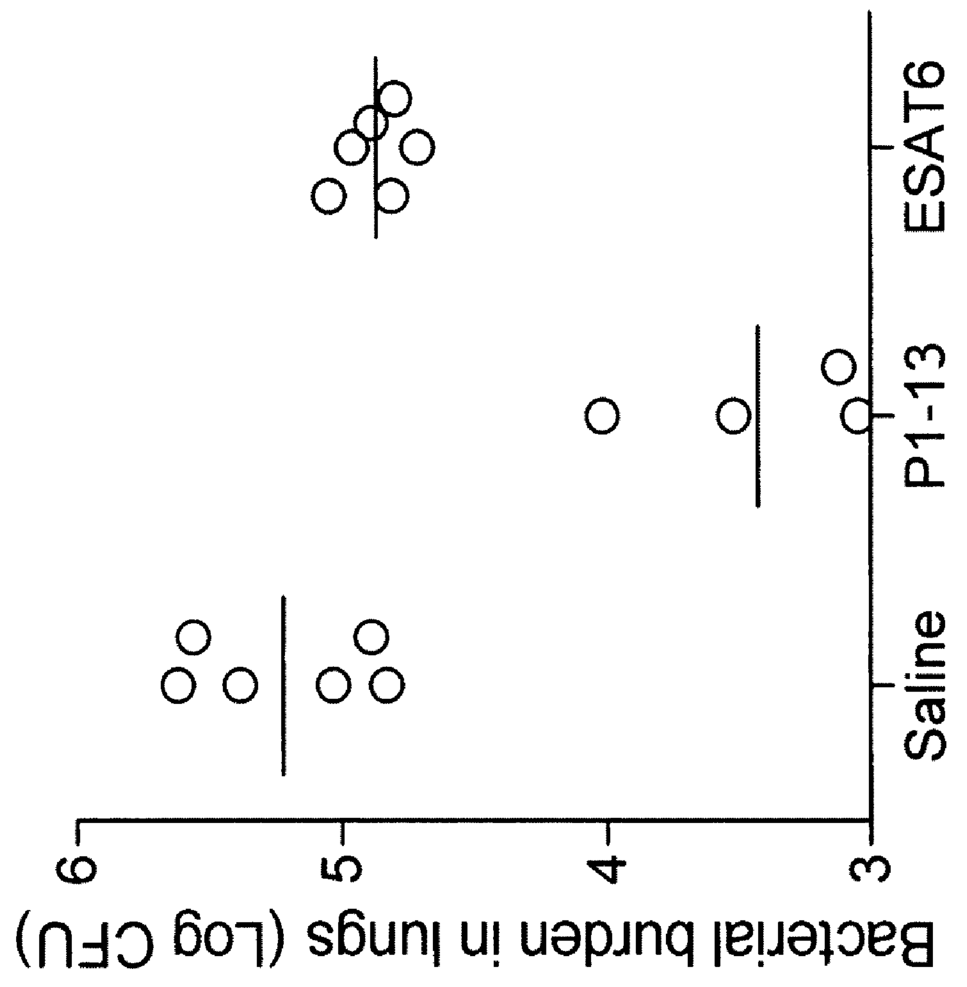
FIG. 12 shows the immunogenicity of a ESAT-6 and ESAT-6 peptide mix. Mice were vaccinated three times at 2-week intervals with either saline (column 1), ESAT-6 peptide mix (P1-P13; column 2), or ESAT-6 (column 3). 6 weeks after the last vaccination, the mice were subjected to an aerosol challenge with virulent *M. tuberculosis* 10 weeks after the challenge, the mice were killed and the bacterial numbers were determined in the lungs.

The results showed that mice vaccinated with ESAT-6 peptide mix not only exhibited a broader recognition of ESAT-6, but were also significant more protected against infection with *M. tuberculosis* compared to mice vaccinated with the recombinant protein ESAT-6 (FIG. 12). Thus, vaccinating with a mix of ESAT-6 peptides leads to a broader recognition of ESAT-6 epitopes which in turn induce a significant higher protection against infection with *M. tuberculosis*, compared to when vaccinating with the recombinant protein ESAT-6.

Example 2

TB10.4

Figure 5:
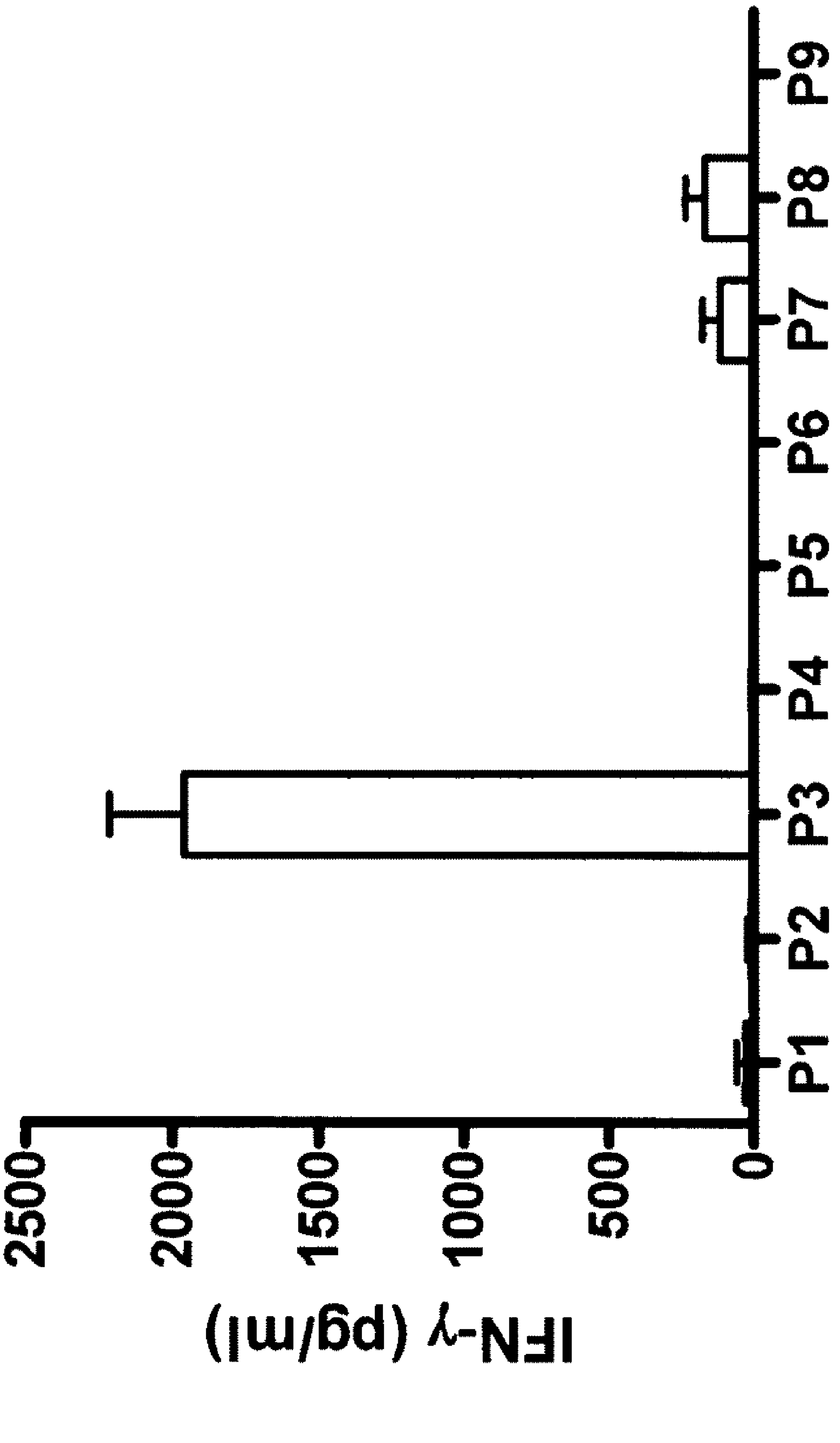
FIG. 5 is a bar chart showing the results of vaccination with recombinant TB10 followed by in vitro stimulation with individual peptides P1-P9. In vitro IFN-γ responses of cells from mice vaccinated three times with DDA/TDB-TB10.4 in DDA/TDB. Cells taken two weeks after final vaccination from blood and stimulated with 0.5 μg/ml of the indicated peptide.

Another protein expressed by *M. tuberculosis* TB10.4 was analyzed as follows. Mice were vaccinated 3 times at 2 weeks interval with recombinant TB10.4, and cells were taken two weeks after final vaccination from blood and stimulated with 0.5 μg/ml of the indicated TB10.4 peptides (FIG. 4, SEQ ID NO:2) and secretion of IFN-gamma (IFN-γ), as assessed by ELISA, was determined. The results showed that vaccinating with TB10.4 mainly induced P3 specific T cells (FIG. 5). P3 therefore constituted a dominant epitope.

Example 3

Figure 6:
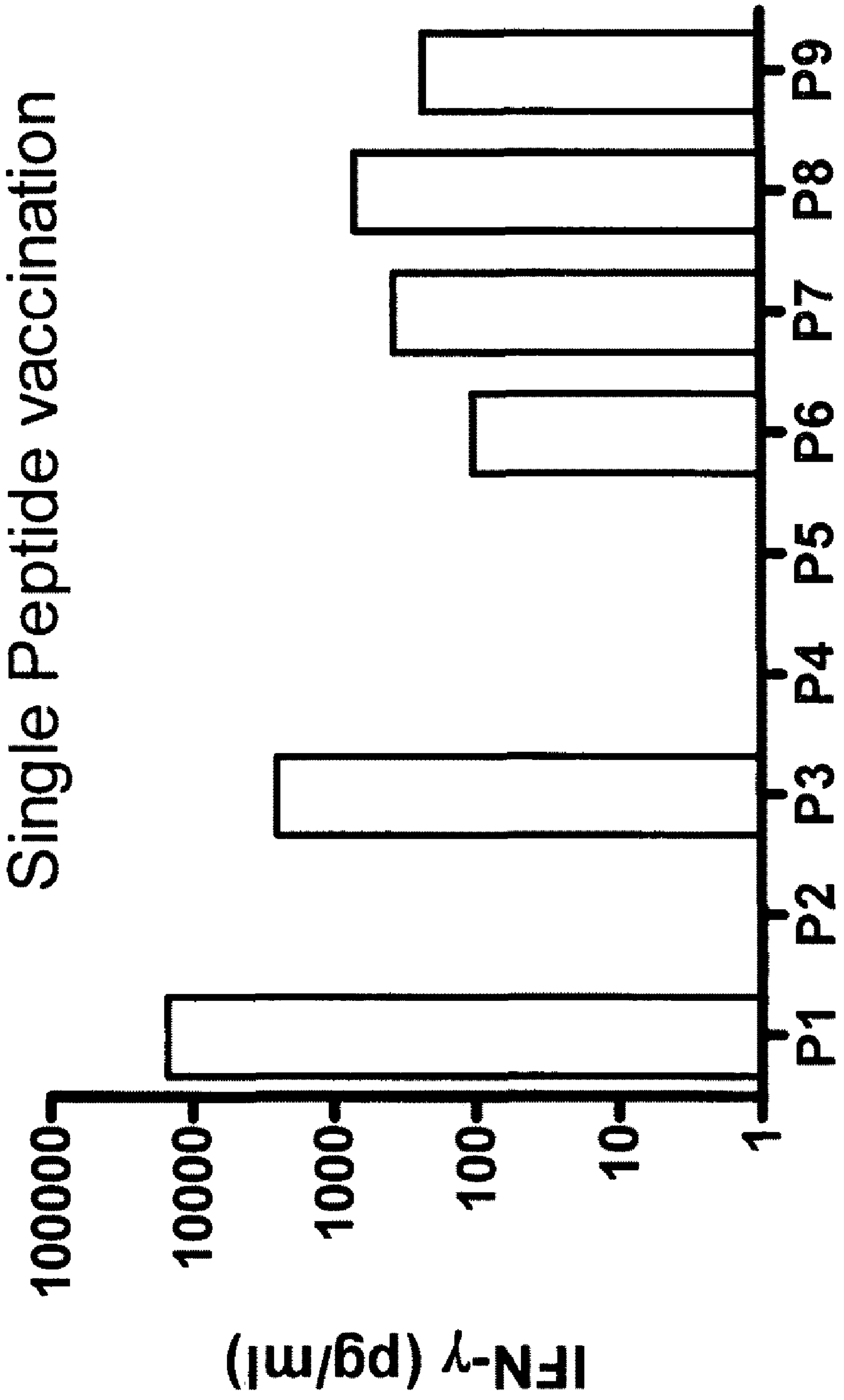
FIG. 6 is a bar chart showing the recognition of TB10.4 peptides P1-P9 following vaccination with individual peptides. In vitro IFN-γ responses of cells from mice vaccinated three times with individual TB10.4 peptides in DDA/TDB. Cells taken two weeks after final vaccination from blood and stimulated with 0.5 μg/ml of the same peptide used for the vaccination and secretion of IFN-γ was determined by ELISA.

To analyze whether the lack of T cells responding to peptides P1 (amino acids 1 to 18 of SEQ ID NO: 2), P2 (amino acids 11 to 28 of SEQ ID NO: 2), P4 (amino acids 31 to 48 of SEQ ID NO: 2), P5 (amino acids 41 to 58 of SEQ ID NO: 2), P6 (amino acids 51 to 68 of SEQ ID NO: 2), and P9 (amino acids 81 to 96 of SEQ ID NO: 2) (and to some degree P7 (amino acids 61 to 78 of SEQ ID NO: 2) and P8 (amino acids 71 to 88 of SEQ ID NO: 2)) was due to these peptide epitopes being subdominant or not immunogenic, animals were vaccinated with the individual TB10.4 peptides (P1-P9). Following vaccination purified lymphocytes were stimulated in vitro the same peptides used for vaccination and secretion of IFN-γ was determined by ELISA. The results showed that other, subdominant (when vaccinating with the recombinant protein TB10.4) peptides were also strongly immunogenic. In particular vaccinating with peptide 1 or 3, or to a lesser degree P7, P8, or P9 induced a specific T-cell response (FIG. 6).

Figure 7:
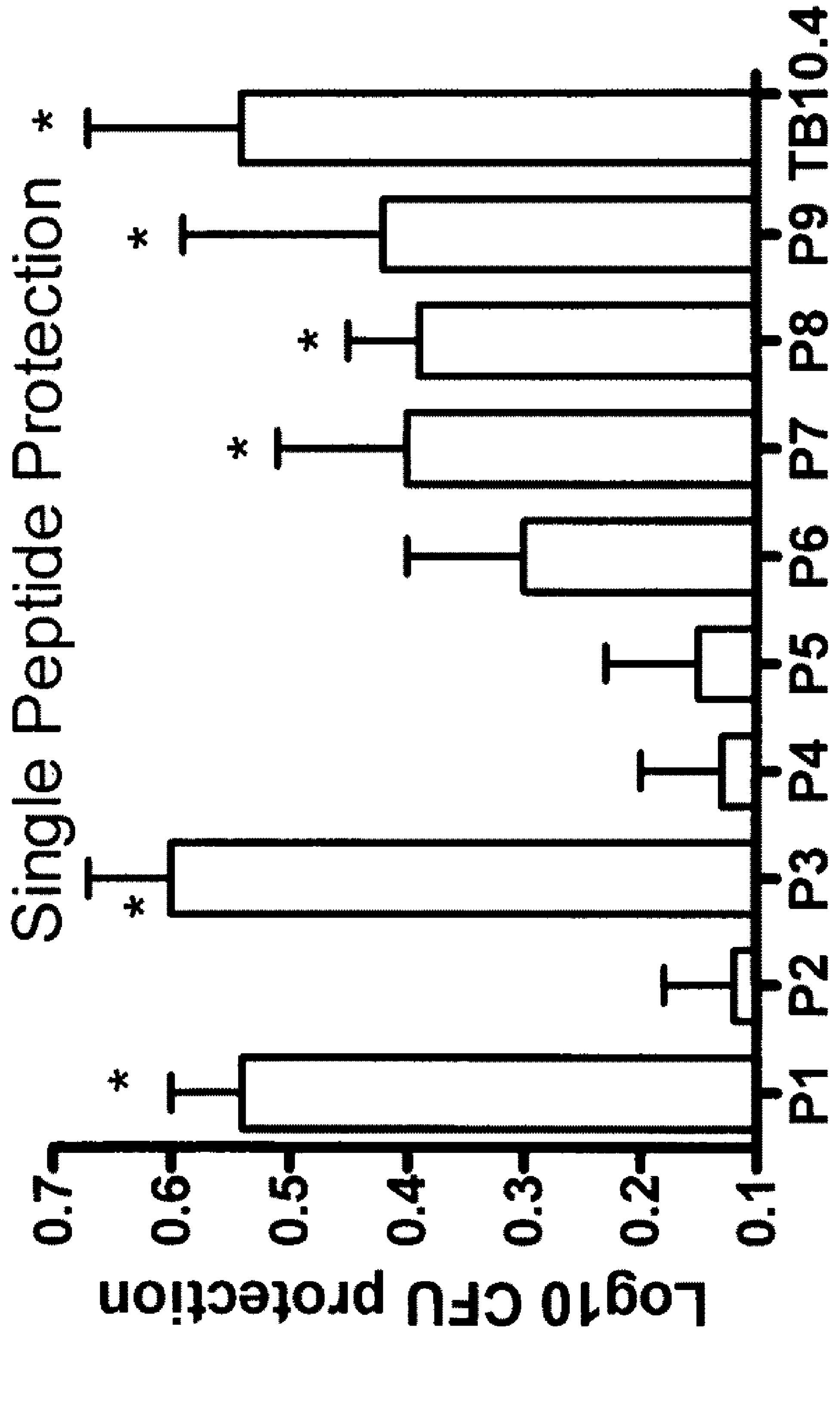
FIG. 7 is a bar chart showing the protective ability of TB10.4 peptides P1-P9. Bacterial burden in vaccinated mice (expressed as $\log_{10}$ in colony forming units (CFU) protection) challenged by the aerosol route with virulent *M. tuberculosis* six weeks after the last vaccination. Six weeks post-challenge, the mice were killed and the bacterial burden (CFU) was measured in the lung. (* $P<0.05$ compared to non-vaccinated mice, ANOVA and Tukey's test).

In addition, the subdominant peptides, in particular P1, P7, P8, P9 all protected against infection with *M. tuberculosis* (FIG. 7). Vaccinating with the dominant peptide epitope P3 (amino acids 21 to 38 of SEQ ID NO: 2) also induced significant protection.

Example 4

Figure 8:
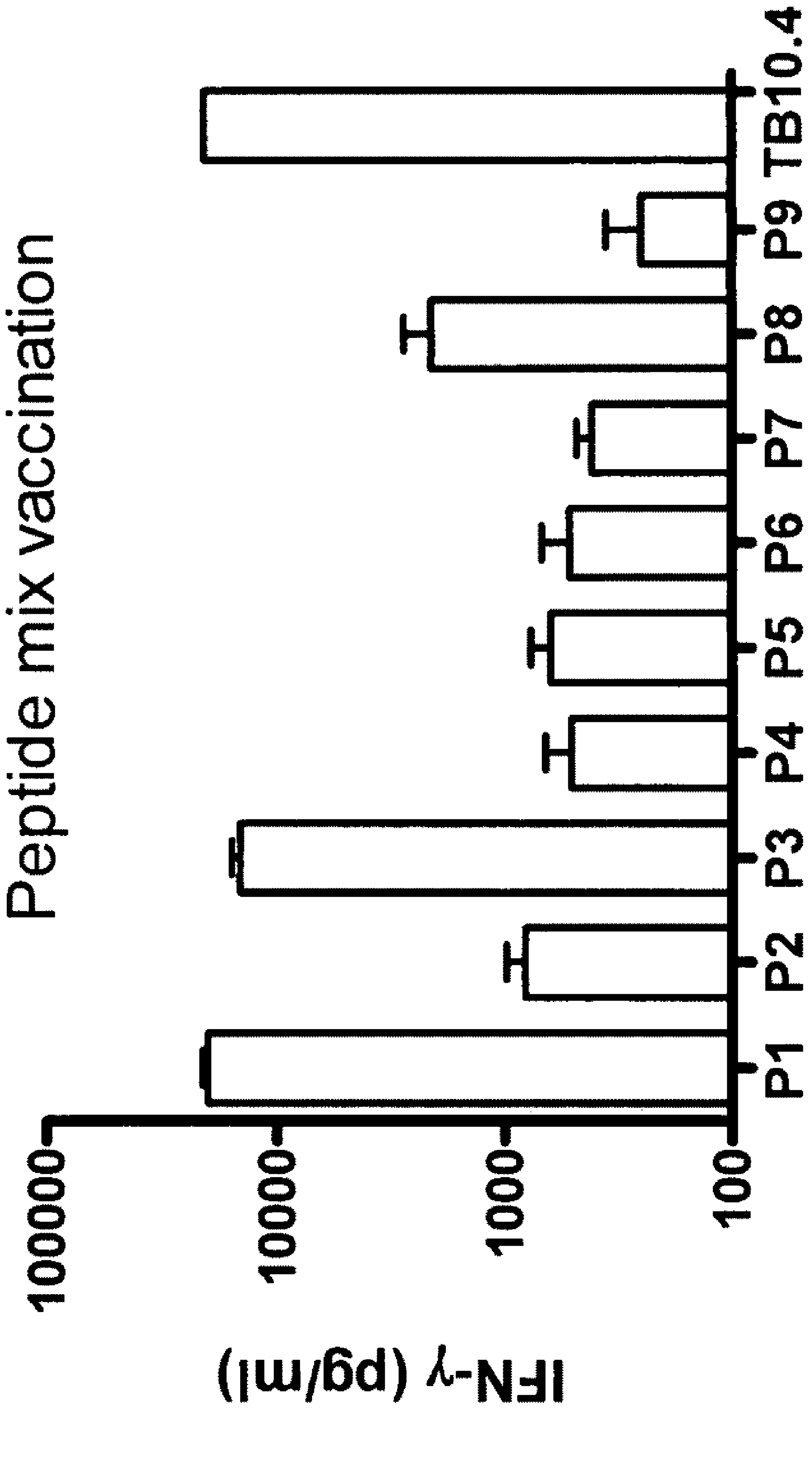
FIG. 8 is a bar chart showing the recognition of TB10.4 peptides P1-P9 after vaccinating with TB10.4 peptide mix. In vitro IFN-γ responses of cells from mice vaccinated three times with DDA/TDB-TB10.4-peptide mix. Cells taken two weeks after final vaccination from blood and stimulated with 0.5 μg/ml peptide or TB10.4 protein as indicated.

Having determined the existence of subdominant epitopes when vaccinating with the recombinant protein TB10.4, whether vaccination with a mix of all overlapping TB10.4 peptides would lead to a broader recognition of P1-P9 compared to mice vaccinated with the recombinant protein TB10.4 was examined. Mice were vaccinated three times at 2-week intervals with a mix of all the peptides, and the immune response was investigated by culturing blood cells with each of the individual TB10.4 peptides P1-P9 (FIG. 8).

The results showed that, in contrast to vaccinating with recombinant protein TB10.4, vaccinating with a mix of TB10.4 peptides (P1-P9) led to a much broader recognition of the peptides. In particular, P1 (amino acids 1 to 18 of SEQ ID NO: 2), P3 (amino acids 21 to 38 of SEQ ID NO: 2), and P8 (amino acids 71 to 88 of SEQ ID NO: 2) were all strongly recognized (FIG. 8).

Example 5

To examine whether the broader response towards TB10.4 was reflected in the protection against infection with *M. tuberculosis*, as compared to the protein induced by vaccination with the recombinant protein TB10.4 [SEQ ID NO:2], mice were vaccinated three times at 2-week intervals with either TB10.4 or TB10.4-peptide mix. 6 weeks after the last vaccination, the mice were subjected to an aerosol challenge with virulent *M. tuberculosis* 6 weeks after the challenge, the mice were killed and the bacterial numbers were determined in the lungs.

Figure 9:
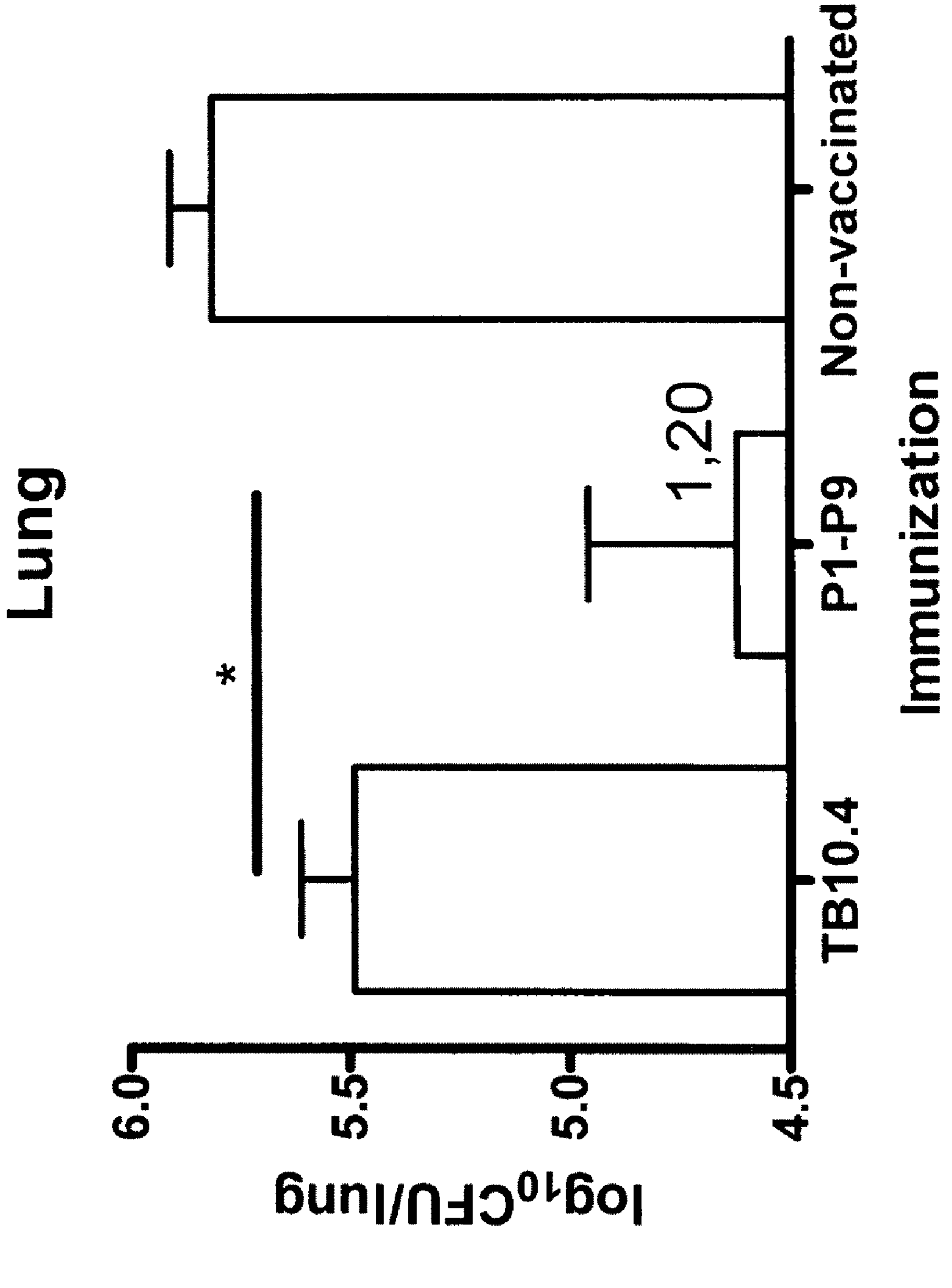
FIG. 9 is a bar chart showing the bacterial burden in TB10.4 or TB10.4-peptide vaccinated mice infected with *M. tuberculosis*. Bacterial burden in vaccinated mice (expressed as $\log_{10}$ in CFU) compared to non-vaccinated controls challenged by the aerosol route with virulent *M. tuberculosis* ten weeks after the first vaccination. Six weeks post-challenge, the mice were killed and the bacterial burden (CFU) was measured in the lung. (* $P<0.05$, ANOVA and Tukey's test).

The results showed that mice vaccinated with TB10.4-peptide mix not only exhibited a broader recognition of TB10.4, but were also significant more protected against infection with *M. tuberculosis* compared to mice vaccinated with the recombinant protein TB10.4 (FIG. 9). Thus, vaccinating with a mix of TB10.4 peptides leads to a broader recognition of TB10.4 epitopes which in turn induce a significant higher protection against infection with *M. tuberculosis*, compared to when vaccinating with the recombinant protein TB10.4[SEQ ID NO:2].

Example 6

CT521

Mice were vaccinated 3 times at 2 weeks interval with recombinant CT521 or a mix of CT521 overlapping peptides (FIG. 10), and cells taken two weeks after final vaccination from blood was stimulated with 0.5 μg/ml of each of the CT521 peptides. Secretion of IFN-gamma, as assessed by ELISA, was determined to examine whether vaccinating with a mix of CT521 peptides leads to a broader recognition of CT521, compared to vaccinating with the recombinant CT521 protein.

REFERENCES

1. Paul, W. 1999. Fundamental Immunology, fourth edition, Lippincott-Raven.
2. Sette, A., and J. Fikes. 2003. *Curr Opin Immunol* 15:461.
3. van der Most, R. G., K. Murali-Krishna, J. G. Lanier, E. J. Wherry, M. T. Puglielli, J. N. Blattman, A. Sette, and R. Ahmed. 2003. *Virology* 315:93.
4. Crowe, S. R., S. J. Turner, S. C. Miller, A. D. Roberts, R. A. Rappolo, P. C. Doherty, K. H. Ely, and D. L. Woodland. 2003. *J Exp Med* 198:399.
5. Wherry, E. J., J. N. Blattman, K. Murali-Krishna, R. van der Most, and R. Ahmed. 2003. *J Virol* 77:4911.
6. Kamath, A. B., J. Woodworth, X. Xiong, C. Taylor, Y. Weng, and S. M. Behar. 2004. *J Exp Med* 200:1479.
7. Olsen, A. W., P. R. Hansen, A. Holm, and P. Andersen. 2000. *Eur J Immunol* 30:1724.
8. McMichael, A. J., and R. E. Phillips. 1997. *Annu Rev Immunol* 15:271.
9. Mowat et al 1991, Immunology 72(3):317-22
10. Lustig et al 1976, Cell Immunol 24(1):164-7
11. Wille-Reece, U., C. Y. Wu, B. J. Flynn, R. M. Kedl, and R. A. Seder. 2005. *J. Immunol.* 174:7676.6
12. Thompson J., et al Nucleic Acids Res 1994 22:4673-4680
13. Ravn, P. et al 1999. J. Infect. Dis. 179:637-645
14. Stryhn, A., et al 1996 Eur. J. Immunol. 26:1911-1918
15. Harboe, M., et al 1998 Infect. Immun. 66:2; 717-723
16. Krogh, T N, Berg, T, & Hojrup, P. (1999). Anal. Biochem. 274, 153-162
17. Gosselin et al., 1992. J. Immunol. 149:3477-3481
18. Babu et al. 1995. Vaccine 13:1669-76.
19. Davidsen et al (2005). Biochim Biophys Acta. 1718:22-31.
20. Munoz et al (2004). Int J Pharm 269:177-84.
21. Kirby & Gregoriadis. 1984. 2:979-984.
22. Pick U. 1981. Arch. Biochem. Biophys. 212:186-194.

All documents cited herein are incorporated by reference. Modification to the embodiments illustrated herein will be appreciated by one of skill in the art and are within the scope of the invention as recited in the following claims.

The invention claimed is:

1. An immunogenic composition against tuberculosis comprising a peptide mixture consisting of at least 13 different adjacent overlapping peptides spanning the full-length amino acid sequence of a *Mycobacterium tuberculosis* protein that is expressed during the chronic phase of the disease and containing dominant and subdominant epitopes, wherein each of the peptides in the peptide mixture is independently selected from a length of 10 amino acids to 30 amino acids in length, said immunogenic composition further comprising cationic liposomes.

2. The immunogenic composition according to claim 1, wherein each of the peptides in the peptide mixture independently has an overlap with the adjacent peptide of 6 to 20 amino acids.

3. The immunogenic composition according to claim 2, wherein each of the peptides in the peptide mixture independently has an overlap with the adjacent peptides of 10 to 12 amino acids.

4. The immunogenic composition according to claim 2, wherein the peptides are independently 12 to 20 amino acids long.

5. The immunogenic composition according to claim 1, wherein the peptides are from a protein selected from a *Mycobacterium tuberculosis* protein selected from the group consisting of early secretory antigenic target (ESAT)6.

6. The immunogenic composition according to claim 1, where the peptides are delivered encapsulated in the liposomes.

7. The immunogenic composition according to claim 1, where one or more of the peptides are lipidated.

8. The immunogenic composition according to claim 1, where each peptide in the peptide mix is mixed or incorporated individually into liposomes prior to making the peptide mixture.

9. The immunogenic composition according to claim 1, where the adjuvant-comprises dimethyldioctadecylammonium bromide/trehalose dibehenate (DDA/TDB).

10. The immunogenic composition according to claim 1, wherein the peptide mixture is a liquid mixture.

11. A method of preparing an immunogenic composition according to claim 1, where the peptide mixture is prepared by a proteolytic cleavage of the protein with two or more proteolytic cleavage agents.

12. The method of preparing an immunogenic composition according to claim 11, where the proteolytic cleavage agent is chosen among proteolytic enzymes selected from the group consisting of trypsin, V-8 protease, AspN and chymotrypsin or chosen among chemical agents selected from the group consisting of CNBr and BNPS-skatole.

13. A method for treatment of *Mycobacterium tuberculosis* infection in an animal comprising administering an effective therapeutic amount of the composition of claim 1 to the animal for inducing an immunogenic response against *Mycobacterium tuberculosis* infection.

14. A method for treatment according to claim 13, wherein the animal is a mammal.

15. A method for treatment according to claim 14, wherein the mammal is a human.

* * * * *